United States Patent
Yamasaki

(10) Patent No.: US 11,660,344 B2
(45) Date of Patent: *May 30, 2023

(54) TRANSDERMAL COLLOIDAL SOLUTION AGENT

(71) Applicant: MEDRx CO., LTD, Higashikagawa (JP)

(72) Inventor: Keiko Yamasaki, Higashikagawa (JP)

(73) Assignee: MEDRX CO., LTD., Kagawa (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/156,244

(22) Filed: May 16, 2016

(65) Prior Publication Data

US 2016/0256552 A1 Sep. 8, 2016

Related U.S. Application Data

(63) Continuation-in-part of application No. PCT/JP2014/080328, filed on Nov. 17, 2014.

(30) Foreign Application Priority Data

| Nov. 17, 2013 | (JP) | JP2013-237494 |
| Feb. 24, 2014 | (JP) | JP2014-033471 |
| Aug. 19, 2015 | (JP) | JP2015-162245 |
| Oct. 7, 2015 | (JP) | JP2015-199676 |
| Dec. 17, 2015 | (JP) | JP2015-246801 |

(51) Int. Cl.
| A61K 8/42 | (2006.01) |
| A61K 31/164 | (2006.01) |
| A61K 31/165 | (2006.01) |
| A61K 31/404 | (2006.01) |
| A61K 31/4164 | (2006.01) |
| A61K 9/70 | (2006.01) |
| A61K 8/49 | (2006.01) |
| A61K 9/06 | (2006.01) |
| A61Q 19/00 | (2006.01) |
| A61K 8/02 | (2006.01) |
| A61P 17/00 | (2006.01) |
| A61K 8/44 | (2006.01) |
| A61Q 19/08 | (2006.01) |
| A61K 47/24 | (2006.01) |
| A61K 31/55 | (2006.01) |
| A61K 47/10 | (2017.01) |
| A61K 9/10 | (2006.01) |
| A61K 47/18 | (2017.01) |
| A61K 9/00 | (2006.01) |
| A61K 31/343 | (2006.01) |
| A61K 31/135 | (2006.01) |
| A61K 31/405 | (2006.01) |
| A61K 31/445 | (2006.01) |
| A61K 31/4196 | (2006.01) |
| A61K 31/13 | (2006.01) |
| A61K 31/473 | (2006.01) |

(52) U.S. Cl.
CPC ............ *A61K 47/24* (2013.01); *A61K 9/0014* (2013.01); *A61K 9/10* (2013.01); *A61K 9/7069* (2013.01); *A61K 31/13* (2013.01); *A61K 31/135* (2013.01); *A61K 31/343* (2013.01); *A61K 31/405* (2013.01); *A61K 31/4196* (2013.01); *A61K 31/445* (2013.01); *A61K 31/473* (2013.01); *A61K 31/55* (2013.01); *A61K 47/10* (2013.01); *A61K 47/18* (2013.01)

(58) Field of Classification Search
None
See application file for complete search history.

(56) References Cited

U.S. PATENT DOCUMENTS

| 6,165,997 A * | 12/2000 | Cohen | A61K 31/66 514/143 |
| 8,568,746 B2 * | 10/2013 | Yamasaki | A61K 31/205 424/400 |
| 2012/0149664 A1 * | 6/2012 | Yamasaki | A61K 8/345 514/78 |
| 2012/0202891 A1 | 8/2012 | Stinchcomb et al. | |

(Continued)

FOREIGN PATENT DOCUMENTS

| EP | 1581172 A2 * | 10/2005 | ............... A61K 8/41 |
| JP | 3313891 B2 | 8/2002 | |
| JP | 2005170833 | 6/2005 | |

(Continued)

OTHER PUBLICATIONS

Azeem et al., "Microemulsions as a Surrogate Carrier for Dermal Drug Delivery," Drug Development and Industrial Pharmacy, 2009, vol. 35, pp. 525-547.

(Continued)

*Primary Examiner* — Layla Soroush
(74) *Attorney, Agent, or Firm* — Morgan, Lewis & Bockius LLP

(57) ABSTRACT

Disclosed is a transdermal absorptive liquid preparation in which a medicament or a salt thereof is colloidally dispersed in propylene glycol or a propylene glycol-containing solvent, whose transdermal permeability of the medicament is excellent, problem of skin irritation is reduced. This transdermal absorptive liquid formulation has a mode of particle diameter at around 100 nm, and an average particle size of 50 to 500 nm. This transdermal absorptive liquid formulation makes marked improvement in the transdermal permeability by further containing an absorption promoter such as triethanolamine.

14 Claims, 6 Drawing Sheets

(56) References Cited

U.S. PATENT DOCUMENTS

| | | |
|---|---|---|
| 2013/0053358 A1 | 2/2013 | Aida et al. |
| 2013/0064868 A1 | 3/2013 | Okazaki et al. |

FOREIGN PATENT DOCUMENTS

| | | |
|---|---|---|
| JP | 201360395 | 4/2013 |
| JP | 2014-152162 | 8/2014 |
| WO | WO 2010/036947 A2 | 4/2010 |
| WO | WO 2011/111384 | 9/2011 |
| WO | WO 2015/072564 | 5/2015 |

OTHER PUBLICATIONS

International Search Report dated Dec. 15, 2014 for International Patent Application No. PCT/JP2014/080328.

Manconi, et al. "Penetration enhancer containing vesicles as carriers for dermal delivery of tretinoin," International Journal of Pharmaceutics, 2011 Nen, 412, p. 37-46.

Santos, et al. "Application of Microemulsions in Dermal and Transdermal Drug Delivery," Skin Pharmacology and Physiology, 2008, vol. 21, pp. 246-259.

Zhao, et al. "Selection of high efficient transdermal lipid vesicle for curcumin skin delivery," International Journal of Pharmaceutics, 2013 Nen 7 Gatsu, 454, p. 302-309.

Jun-Bom Park et al., "Enhanced Transdermal Delivery and Optimization of Nano-Liposome Preparation Using Hydrophilic Drug", Journal of Korean Pharmaceutical Sciences, vol. 42, No. 2, Apr. 1, 2012, pp. 57-63.

Supplemental European Search Report received in related European Application No. 14862046.1 dated Oct. 18, 2016 in 17 pages.

New Techniques and New Dosage Forms of Drugs, 2nd Edition, in part p. 532, the 7th line from the bottom to p. 535, line 27 (2005).

\* cited by examiner

TRANSDERMAL COLLOIDAL SOLUTION AGENT

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention relates to a novel transdermal absorptive liquid formulation. Specifically, the present invention relates to an external preparation containing a medicament and phosphatidyl choline.

Description of the Related Art

There are various methods to make a medicament permeate through the skin. In general, the medicament is completely dissolved in a solvent, and the concentration gradient or effect of an absorption promoter ensure the permeability of the medicament. Alternatively, it is known that phosphatidyl choline is used to form a micelle, and to have a medicament permeate through the skin (Patent Document 1 and 2).

As an external liquid preparation containing phosphatidyl choline, a liquid preparation in which L-carnitine is contained to achieve an excellent absorbability of phosphatidyl choline (Patent Document 1), and an oil-in-water emulsion liquid preparation of ropinirole hydrochloride (Patent Document 2) are known.

The transdermal absorptive formulation may occasionally cause cutaneous irritation depending on a sort of the medicament. Therefore, suppressing the cutaneous irritation should be considered when the dosage form is designed. For example, cholesterol has been used as a cutaneous irritation suppressing agent of donepezil (Patent Document 3).

On the other hand, a transdermal absorptive liquid formulation in which phosphatidyl choline is dispersed in propylene glycol (patent document 4) is known as a technique to make various medicaments absorb transdermally. The technique has a simple composition, is able to apply various medicaments, and exhibits excellent effect on improvement of the transdermal permeability. However, some medicament is highly desired to be absorbed in a very short time, thus further improvement in percutaneous permeability has been required.

On the other hand, it is proposed that adding a transdermal absorption accelerator such as higher fatty acid, higher alcohol, and fatty acid ester in order to improve transdermal absorbability (for example Patent Document 5 and 6). However a technique to shorten a transdermal absorption lag time, and improve transdermal absorbability of colloidal liquid formulation containing propylene glycol and phosphatidyl choline has not been proposed.

PATENT DOCUMENTS

Patent Document 1: WO2011/024354
Patent Document 2: WO2011/111384
Patent Document 3: WO2011/136288
Patent Document 4: WO2015/072564
Patent Document 5: Japanese Patent Publication No. 2014-152162
Patent Document 6: Japanese Patent Publication No. 2013-60395

Non Patent Documents

Non patent Document 1: P. Santos et al, Skin Pharmacol Physiol 2008; 21:246-259
Non patent Document 2: Adenan Azeem et al, Drug Development and Industrial Pharmacy, 35: 252-547, 2009

SUMMARY OF THE INVENTION

An object of the present invention is to provide a transdermal absorptive liquid formulation which exhibits high transdermal permeability of a medicament, and whose cutaneous irritation is suppressed.

Also, an object of the present invention is to provide a transdermal absorptive formulation having a shortened transdermal absorption lag time, and being able to achieve a maximum skin permeation rate immediately. Another object of the present invention is to provide a transdermal absorptive liquid formulation which has a reduced skin irritation and is suitable for prolonged and/or chronic administration.

The present inventor found that the formulation in which a medicament and phosphatidyl choline are colloidally dispersed in Propylene glycol or a propylene glycol-containing solvent as particles having 50-500 nm diameter exhibits extremely excellent transdermal permeability and maintains said excellent permeability compared to a solution in which a medicament is completely dissolved and exists in a molecular state. The inventor further found that the effects are doubled by adding an alkanolamine. In addition, adding higher alcohol to the formulation can achieve a shortened transdermal absorption lag time and high plasma concentration of the medicament.

The subject matters of the present invention are as follows.

(1) A transdermal absorptive colloidal liquid formulation wherein, a medicament or a salt thereof is colloidally dispersed in propylene glycol or a propylene glycol-containing solvent in the presence of phosphatidyl choline, and contains no hydrophobic solvent.
(2) The transdermal absorptive colloidal liquid formulation according to the above item (1), further comprising an alkanolamine.
(3) The transdermal absorptive colloidal liquid formulation according to the above items (1) or (2), wherein the alkanolamine is triethanolamine.
(4) The transdermal absorptive colloidal liquid formulation according to any one of the above items (1) to (3), wherein the medicament contains a six-membered ring skeleton and a nitrogen containing group in a structure thereof.
(5) The transdermal absorptive colloidal liquid formulation according to any one of the above items, wherein an average particle diameter of the colloidal liquid is 50-500 nm.
(6) The transdermal absorptive colloidal liquid formulation according to any one of the above items (1) to (5), wherein a content of the phosphatidyl choline is from 0.1 to 5 w/w %.
(7) The transdermal absorptive colloidal liquid formulation according to any one of the above items (1) to (6), wherein the phosphatidyl choline is an unsaturated phosphatidyl choline.

(8) The transdermal absorptive colloidal liquid formulation according to any one the above items (2) to (7), wherein a content of the alkanolamine is from 0.01~10 w/w %.
(9) The transdermal absorptive colloidal liquid formulation according to any one of the above items (1) to (8), wherein the phosphatidyl choline is at least one selected from an egg yolk phosphatidyl choline and soybean phosphatidyl choline.
(10) A method for preparing a transdermal absorptive colloidal liquid formulation in which a medicament or a salt thereof is colloidally dispersed in propylene glycol-containing solvent, comprising a step of mixing the medicament or a salt thereof which is in dissolved state in propylene glycol or the propylene glycol-containing solvent and phosphatidyl choline which is in dissolved state in propylene glycol or the propylene glycol-containing solvent.
(11) The method for preparing the transdermal absorptive colloidal liquid formulation according to the above item (10), further comprising a step of adding alkanolamine.
(12) The method for preparing the transdermal absorptive colloidal liquid formulation according to the above item (10) or (11), wherein the alkanolamine is triethanolamine.
(13) The method for preparing the transdermal absorptive colloidal liquid formulation according to any one of the above items (10) to (12), wherein an average particle diameter of the colloidal liquid is 50-500 nm.
(14) The method for preparing the transdermal absorptive colloidal liquid formulation according to any one of the above items (10) to (13), wherein a content of the phosphatidyl choline is from 0.1 to 5 w/w %.
(15) The method for preparing the transdermal absorptive colloidal liquid formulation according to any one of the above items (10) to (14), wherein the phosphatidyl choline is an unsaturated phosphatidyl choline.
(16) The method for preparing the transdermal absorptive colloidal liquid formulation according to any one of the above items (10) to (15), wherein a content of alkanolamine is from 0.01 to 10 w/w %.
(17) The method for preparing the transdermal absorptive colloidal liquid formulation according to any one of the above items (10) to (16), wherein phosphatidyl choline is at least one selected from an egg yolk phosphatidyl choline and soybean phosphatidyl choline.
(18) A liquid type adhesive patch, wherein the transdermal absorptive colloidal liquid formulation according to any one of the above items (1) to (19) is impregnated into a foamed matrix.
(19) The liquid type adhesive patch according to the above item (18), wherein the foamed matrix is urethane form.
(20) A use of phosphatidyl choline for colloidally dispersing a medicament or a salt thereof in propylene glycol or propylene glycol-containing solvent.
(21) The use according to the above item (20), wherein the phosphatidyl choline is at least one selected from an egg yolk phosphatidyl choline and soybean phosphatidyl choline.
(22) A transdermal absorptive liquid formulation comprising a medicament or a salt thereof, propylene glycol, phosphatidyl choline, and a higher alcohol.
(23) The transdermal absorptive liquid formulation according to the above item (22), wherein the higher alcohol is oleyl alcohol and/or isostearyl alcohol.
(24) The transdermal absorptive liquid formulation according to the above item (22), wherein an amount of the higher alcohol is 0.1 to 10 weight % based on a total weight of the transdermal absorptive liquid formulation.
(25) The transdermal absorptive liquid formulation according to the above item (22), wherein an amount of the higher alcohol is 0.2 to 5 weight % based on a total weight of the transdermal absorptive liquid formulation.
(26) The transdermal absorptive liquid formulation according to the above item (22), wherein an amount of the propylene glycol is 40 to 98 weight % based on a total weight of the transdermal absorptive liquid formulation.
(27) The transdermal absorptive liquid formulation according to the above item (22), wherein an amount of the propylene glycol is 60 to 90 weight % based on a total weight of the transdermal absorptive liquid formulation.
(28) The transdermal absorptive liquid formulation according to the above item (22), wherein an amount of the phosphatidyl choline is 0.1 to 5 weight % based on a total weight of the transdermal absorptive liquid formulation.
(29) The transdermal absorptive liquid formulation according to the above item (22), further comprising an alkanolamine.
(30) The transdermal absorptive colloidal liquid formulation according to the above item (31), wherein the alkanolamine is triethanolamine.

Effects of the Invention

The colloidal liquid formulation of the present invention has an extremely improved transdermal permeability and has achieved fast and persistent permeability by colloidally dispersing a medicament. Therefore, it is possible to achieve a high blood concentration same as when an oral preparation is administrated. Additionally, the cutaneous irritation can be markedly suppressed by administrating as the colloidal liquid preparation of the present invention even if the medicament is known to cause cutaneous irritation. The transdermal absorptive liquid formulation has a short transdermal absorption lag time and is able to achieve a maximum skin permeation rate immediately. Furthermore, skin irritation is significantly reduced even if it is a medicament with which skin irritation due to increase of skin permeation rate has been reported in conventional transdermal formulation. Thus, the transdermal absorptive liquid formulation described herein is suitable for prolonged and/or chronic administration.

BRIEF DESCRIPTION OF THE DRAWINGS

FIG. 4 shows the particle size distribution of the colloidal liquid formulation containing ramelteon prepared in Example 2a.
FIG. 5 is a graph showing the result of the blood concentration evaluation test of the colloidal liquid formulation containing ramelteon prepared in Example 2a.

DETAILED DESCRIPTION OF THE PREFERRED EMBODIMENT

Figure 1:
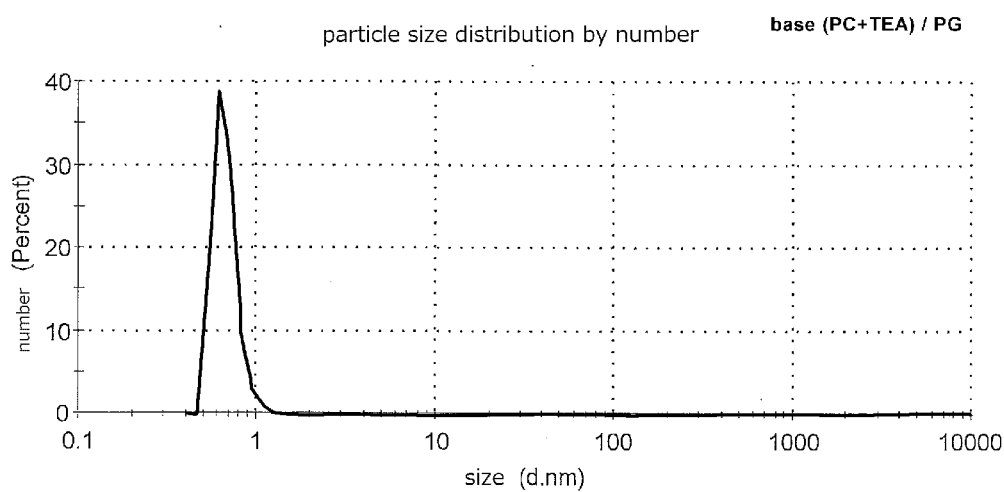
FIG. 1 shows the particle size distribution of the solution prepared in Reference Preparation Example.

The present invention relates to a transdermal absorptive colloidal liquid formulation in which a medicament and phosphatidyl choline are dispersed in propylene glycol or a propylene glycol-containing solvent, and in some embodiments, further comprising alkanolamine. In some embodiments, the liquid formulation may further comprise oleyl alcohol and/or isostearyl alcohol (16-methyl heptadecene-1-ol).

The present invention also relates a method for preparing the formulation. The term "propylene glycol-containing solvent" in this specification denotes propylene glycol to which a solubilizing agent such as water and/or a hydrophilic solvent is dissolved in and mixed as described below in detail.

The term "colloidal dispersion" in this description denotes a liquid exhibiting a clear Tyndall phenomenon by irradiation with red laser light. The average particle diameter of the dispersoid (colloidal particles) in the colloidal dispersions of the present invention is from 0.05 to 0.5 μm, preferably from 0.05 to 0.2 μm. in addition, it has a mode of particle diameter around 0.1 μm (from 0.04 to 0.15 μm). This colloidal dispersion was stable and aggregation over time and the like were not observed.

Any of a neutral medicament, a basic medicament, and an acidic medicament can be utilize as the "medicament". The term "medicament" in this description includes its pharmaceutically acceptable salt. The "neutral medicament" means a non-ionic medicament such as a medicament having a hydroxyl group or an amide group. The "basic medicament" means a medicament having a primary, secondary or tertiary amino group and exhibiting basicity as whole compound. The "acidic medicament" means a medicament having carboxyl group or the like and exhibiting acidity as whole compound. The neutral medicament or the basic medicament is particularly preferred as the medicament, because they particularly exhibit the significant effects of the present invention such as excellent skin permeability and stability of the solution.

A compound having a six-membered ring skeleton and a nitrogen-containing group in its structure can be preferably utilized as the medicament. When the medicament has such a structure, a stable colloid to be formed, thus the effect of the present invention to improve the skin permeability is expressed significantly. Six-membered ring in the six-membered ring skeleton can be either homocyclic rings or heterocyclic ring. Said six-membered ring includes a ring having aromaticity, a saturated or unsaturated aliphatic ring which may have a bridged structure. Non-limiting examples of the six-membered homocyclic rings are shown as (a) to (c), non-limiting examples of the six-membered heterocyclic rings are shown as (d) to (f) below.

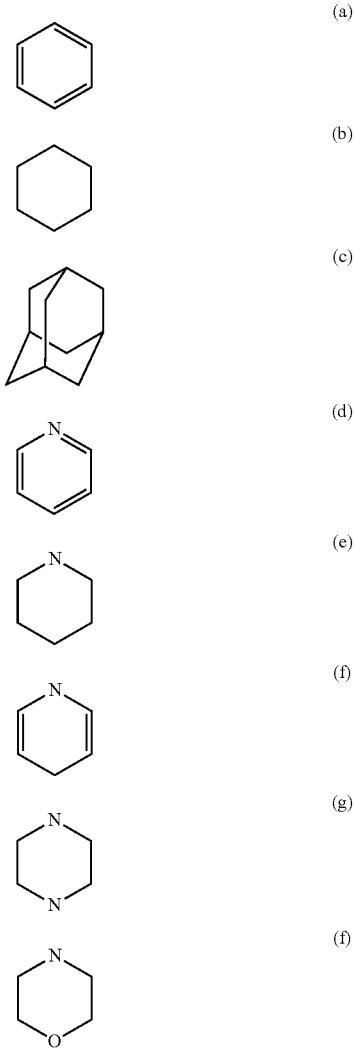

An amino group, an imino group, an amido group, a cyano group, a nitro group can be exemplified as the nitrogen-containing group. The nitrogen-containing group may be bound to the six-membered ring skeleton described above via an arbitrary organic group.

In case where the medicament contains six-membered ring having nitrogen such as pyridine, piperidine, and peperaine, said six-membered ring can also be recognized as the nitrogen-containing group. In other words, if nitrogen is contained as one of the constituent elements of the six-membered ring skeleton, the medicament is not required to contain other nitrogen-containing group as well.

It is preferred that the six-membered ring forms a structure represented by the following formula I-a or I-b, as the result of at least two adjacent carbon atoms have a substituent.

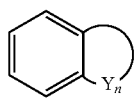

(I-a)

In formula I-a, Y is same or different, and represent a carbon atom, a nitrogen atom, an oxygen atom, or a sulfur atom, n represents an integer of 3-5. Each atom represented by Y bind each other via a single bond or a double bond.

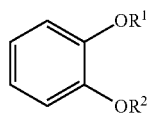

(I-b)

In formula I-b, $R^1$ and $R^2$ are same or different, and represent an organic group which may bind to each other or to other substituents to form a ring or a hydrogen tom.

In some embodiments, the value of n is preferably 3 or 4, most preferably 3, in case where the medicament contains the structure represented by formula I-1. When n is 3, the structure represented by the formula I-a can be, for example, a condensed ring structure comprising a six-membered ring and a five-membered ring as shown in Table 2. Specifically, a homocyclic ring such as indane, indene and the like; a heterocyclic ring containing an oxygen atom such as benzofurin, isobenofurin, benzofuran, isobenzofuran, and the like; a heterocyclic ring containing two oxygen atoms such as benzodioxole and the like; a heterocyclic ring containing a nitrogen atom such as indoline, indole, isoindole, and the like; a heterocyclic ring containing two nitrogen atoms such as indazole, benzoimidazoline and the like; a heterocyclic ring containing a sulfur atom such as benzothiophene and the like; a heterocyclic ring containing an oxygen atom and a nitrogen atom such as benzoxazol, benzisoxazol, and the like; a heterocyclic ring containing a nitrogen atom and a sulfur atom such as benzothiadiazole and the like can be exemplified.

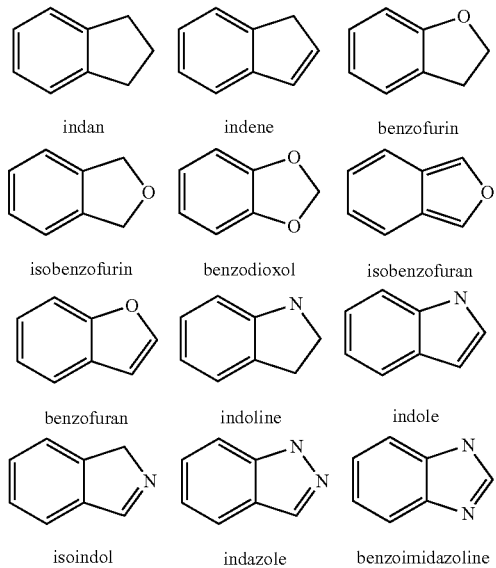

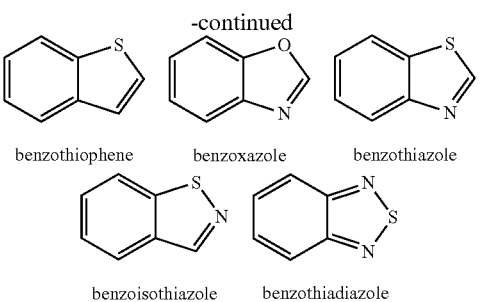

As the medicament containing the structure represented by the formula I-a and n is 3, a neutral medicament containing indane structure such as ramelteon, and the like; a basic medicament containing indane structure such as rasagiline, donepezil, and the like; a basic medicament containing isobenzofurin structure such as escitalopram, galantamine, and the like; a neutral medicament containing benzofurin structure such as ramelteon, and the like; a basic medicament containing benzofurin structure such as morphine, oxycodone, and the like; a basic medicament containing benzodioxole structure such as paroxetine, and the like; a basic medicament containing indoline structure such as ropinirole, and the like; an acidic medicament containing indole structure such as indomethacin, and the like; a basic medicament containing indole structure such as pergolide, bromocriptine, ondansetron, and the like; a basic medicament containing indazol structure such as granisetron, and the like; a basic medicament containing benzothiophene structure such as raloxifene, zileuton, and the like; a basic medicament containing benzoisothiazole structure such as lurasidone, and the like; a basic medicament containing benzothiadazole structure such as tizanidine, and the like can be exemplified.

In some embodiments, when n is 4, the structure represented by formula I-a has a structure in which two six-membered rings are condensed. Specifically, a naphthalene skeleton, a quinolone skeleton, an isoquinoline skeleton, a cinnolin skeleton, a quinazoline skeleton, a quinoxaline skeleton, a phthalazine skeleton, a chroman skeleton, and the like can be exemplified. As the medicament containing such a structure, apomorphine, morphine, oxycodone, pergolide, bromocriptine, propranolol, butorphanol, rotigotine, aripiprazole, doxazosin, quinapril, esuprone, procaterol, azelastine, chlorpromazine, and the like can be exemplified.

In some embodiments, when n is 5, the structure represented by formula I-a is a condensed ring comprising a six-membered ring and a seven-membered ring. As the medicament containing such a structure, imipuran, flurazepam, diltiazem, ketotifen, and the like can be exemplified.

As the medicament containing the structure represented by the formula I-b, a basic medicament in which both $R^1$ and $R^2$ are hydrogen atoms such as apomorphine, dopamine, Isoprenaline, and the like; a basic medicament in which both $R^1$ and $R^2$ are aliphatic hydrocarbon groups such as donepezil, verapamil, oxypertine, and the like; a basic medicament in which $R^1$ is a hydrogen atom or an aliphatic group, $R^2$ is an aliphatic group which forms a ring together with at least two carbon atoms constituting the six-membered ring such as galantamine, morphine, oxycodone, and the like can be exemplified.

Additionally, as the medicament containing a six-membered ring skeleton and a nitrogen-containing group, a basic medicament containing pyridine structure such as nicametate, betahistine, and the like; a basic medicament containing piperidine skeleton such as difenidol, fentanyl, morphine, oxycodone, apomorphine, donepezil, methylphenidate, eperisone, pridinol, trihexyphenidyl, pyridoxal, and the like; a basic medicament containing dihydropyridine skeleton such as nicardipine, benidipine, efonidipine, and the like; a basic medicament containing piperidine structure such as flunarizine, and the like; a basic medicament containing morpholine skeleton such as timolol, and the like; a basic medicament containing adamantane skeleton such as amantadine, memantine, vildagliptin, and the like; a basic medicament containing benzene ring and a nitrogen-containing ring such as tolazoline, clemastine, rilmazafone, and the like; a basic medicament containing benzene ring and a secondary amino group such as bisoprolol, metoprolol, alprenolol, methamphetamine, tulobuterol, and the like; a neutral medicament containing benzene ring and a secondary amino group such as tolbutamide, glibenclamide, acetohexamide, and the like; a basic medicament containing benzene ring and a tertiary amino group such as oxybutynin, neostigmine, lidocaine, and the like; a basic medicament containing benzene ring and a primary amino group such as procaine, and the like can be exemplified.

In some embodiments, any of low-molecule, middle-molecule, and high molecule compound having physiological activity, which usually have one or more polar group can be utilize. For example, a medicament containing indane structure such as ramelteon, rasagiline, and donepezil; a medicament containing indole structure such as rizatriptan, sumatriptan, naratriptan, zolmitriptan, eletriptan, almotriptan; a medicament containing piperidine structure such as donepezil, trihexyphenidyl, perisoxal; a medicament containing benzofuran structure such as morphine, oxycodone, galantamine; a medicament containing isobenzofuran structure such as escitalopram; a medicament containing benzodioxole structure such as paroxetine; a medicament containing indole structure such as indometacin, pergolide, bromocriptine, ondansetron; a medicament containing indazole structure such as granisetron; a medicament containing benzoisothiazole structure such as lurasidone; a medicament containing benzothiadiazole structure such as tizanidine; a medicament containing adamantane structure such as amantadine, memantine, vildagliptin; an opioid pain reliever such as tramadol, morphine, oxycodone, hydromorphone; a histidine derivative such as anserine; a salicylic acid derivative such as aspirin, methyl salicylate; a peptide; a sugar chain are exemplified. The medicament can be a combination of two or more medicaments.

The medicament can be used alone or a combination of two or more medicaments. The contents of the medicament can be selected from, for example, in the range from 0.1 to 25 weight % relative to total weight of the liquid formulation.

In some embodiments, the content of the medicament can be selected from the range of 0.1 to 10 w/w %, preferably the range of 0.5 to 5 w/w %.

Phosphatidyl choline is a collective term of a compound represented by formula (II), usually provided as mixture having different types and combinations of $R^1$ and $R^2$.

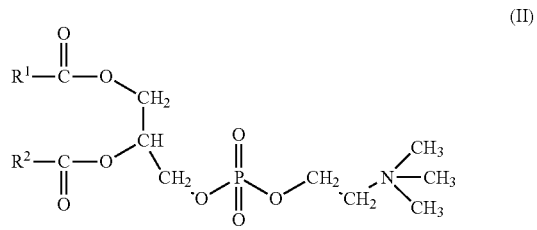

In formula II, $R^1$ and $R^2$ are identical or different each other, and each is a $C_{12-22}$ hydrocarbon group. In some embodiments, an unsaturated phosphatidyl choline in which at least one of $R^1$ and $R^2$ is an unsaturated hydrocarbon group can be utilized in the present invention. Though it may be possible that a saturated hydrocarbon group such as palmityl group (16:0), stearyl group (18:0) is included as $R^1$ and $R^2$, the unsaturated phosphatidyl choline which can be utilize in the present invention contains less than 80% of the saturated hydrocarbon group, preferably less than 70% of the saturated hydrocarbon group, more preferably less than 60% of the saturated hydrocarbon group, most preferably less than 50% of the saturated hydrocarbon group. Palmitoyl group (16:1), oleyl group (18:1), linoleyl group (18:2), linolenyl group (18:3) can be exemplified as the unsaturated hydrocarbon group. It is preferred that the content of the unsaturated hydrocarbon group having 18 carbon atoms such as oleyl group, linoleyl group, linolenyl group, and the like is equal to or more than 20%, more preferably equal to or more than 30%, particularly preferably equal to or more than 40%. With the use of the unsaturated phosphatidyl choline, a stable colloidal dispersion exhibiting excellent transdermal permeability can be prepared.

In some embodiments, a highly purified phosphatidyl choline which can be utilize in the present invention is a naturally derived phosphatidyl choline such as a soybean lecithin, an egg yolk lecithin, and whose content of the phosphatidyl choline is equal to or more than 95%. It is not preferable to use a chemically and/or biologically modified phosphatidyl choline such as a hydrogenated phosphatidyl choline obtained from hydrotreatment or a lysophosphatidyl choline is used, because stable colloidal dispersion may not be obtained. However, of the chemically or biologically modified phosphatidyl choline, a highly purified phosphatidyl choline having a high unsaturation degree (for example, the iodine value is 20 or more, and content of lysolecithin is less than 10%) such as a partial hydrogenated product of a naturally derived phosphatidyl choline can be utilized as the "unsaturated phosphatidyl choline" of the present invention. If the colloid is not formed, enhancing effects to the transdermal absorbability of the medicament is limited.

In some embodiments, the concentration of phosphatidyl choline is selected from, usually in the range of 0.1 to 5 w/w %, preferably 0.1 to 3.0 w/w % or 0.2 to 3.0 w/w %, more preferably 0.1 to 2.0 w/w % or 0.3 to 2.0 w/w %, particularly preferably 0.2 to 1.5 w/w % or 0.3 to 1.5 w/w %. In some embodiments, it is preferred that the concentration of phosphatidyl choline is not less than 0.1 w/w %, because stable colloidal dispersion may not be formed. Adding phosphatidyl choline to more than 5 w/w % does not cause the improvement of transdermal permeability depending on the increase in the phosphatidyl choline concentration.

The liquid formulation of the present invention in which a medicament and phosphatidyl choline are colloidally dispersed in propylene glycol or propylene glycol-containing solvent exhibits excellent preservation stability and transdermal permeability.

In some embodiment, the liquid formulation of the present invention further contains a higher alcohol. By containing the higher alcohol, transdermal permeability of the medicament is improved. As the higher alcohol, $C_{14-20}$ saturated or unsaturated aliphatic mono-alcohols can be exemplified. As the higher alcohol, oleyl alcohol and/or isostearyl alcohol are most preferable. By containing oleyl alcohol and/or isostearyl alcohol, transdermal permeability of the medicament is improved dramatically. Especially, the transdermal absorption lag time is reduced to achieve the maximum skin permeation rate promptly. The concentration of oleyl alcohol and/or isostearyl alcohol is, for example 0.1 to 10 weight %, preferably 0.2 to 5 weight %, relative to total weight of the liquid formulation. In some embodiments, if content of oleyl alcohol and/or isostearyl alcohol is less than 0.1 weight %, it may be hard to obtain transdermal permeation promoting effect. Even if oleyl alcohol and/or isostearyl alcohol is added more than 5 weight %, improvement of skin permeability depending on concentration is not be observed. In other embodiments, the transdermal absorptive liquid formulation of the present invention contains a medicament and phosphatidyl choline in propylene glycol or propylene glycol-containing solvent and further contains oleyl alcohol and/or isostearyl alcohol (16-methyl heptadecene-1-ol).

Though both oleyl alcohol and isostearyl alcohol has excellent ability to enhance transdermal permeation in combination with the liquid formulation containing phosphatidyl choline and propylene glycol, oleyl alcohol has an especially excellent effect. Therefore, it is preferred to contain at least oleyl alcohol. When oleyl alcohol and isostearyl alcohol are used jointly, their mixing ration is not especially limited, can be selected arbitrarily.

In some embodiments, the liquid formulation of the present invention further contains an alkanolamine. The transdermal permeability of the medicament is further improved by containing an alkanolamine. The transdermal permeability of the medicament is improved spectacularly by further containing an alkanolamine as an absorption promoter. Primary, secondary or tertiary alkanolamine having 2 to 12 carbon atoms can be used as the alkanolamine. Among these, secondary or tertiary alkanolamine are preferred, tertiary alkanol amine is particularly preferred. Specifically, diethanolamine, triethanolamine, diisopropanolamine, and triisopropanolamine can be exemplified. Triethanolamine is particularly preferred, since transdermal permeability promoting effect is excellent, and it exhibits an excellent effect of accelerating transdermal permeation.

The concentration of alkanolamine is selected from the range of 0.01 to 10 w/w %, depending on the properties of the medicament. In most of the medicament, the transdermal permeability promoting effect is remarkably exhibited in the range of 1 to 8 w/w %, particularly 2 to 5 w/w %. In some embodiments, the transdermal permeability promoting effect is remarkably exhibited in the range of 0.1 to 5 w/w %, particularly 0.2 to 2 w/w %. However, in some embodiments, the concentration of alkanolamine may be 1 w/w % or less. Donepezil hydrochloride described below is an example of the case.

Property of the liquid formulation of the present invention will depend on both property of the dissolved medicament or its salt and additive amount of the alkanolamine. Though preferred property of the liquid formulation of the present invention is weak alkaline, some medicaments are unstable under alkaline condition. Therefore, the additive amount of alkanolamine can be appropriately adjusted. For example, in case of donepezil hydrochloride, desirable additive amount of triethanolamine is 0.01 to 0.5 w/w %, because adding it in excess to 1% causes precipitation and aggregation of the crystal. As just described, the pH of the liquid formulation can be adjusted appropriately with the additive amount of alkanolamine depending on stability of the medicament.

"Propylene glycol" used in the present invention is not particularly limited, and commercially available ones can be used. The colloidal dispersion of the present invention can be prepared by mixing the medicament of the dissolved state in propylene glycol with phosphatidyl choline of the dissolved state in propylene glycol as described below in detail. Some salts of the basic medicament have low solubility in propylene glycol (for example, less than 1 w/w %), thus the medicament can't be dissolved in propylene glycol at a desired quantity. In such occasion, a solubilizing agent such as water and polyethylene glycol is added in propylene glycol to from propylene glycol-containing solvent. Then, the medicament of dissolved state in propylene glycol can be prepared by dissolving the medicament to said propylene glycol-containing solvent. The additive amount of the solubilizing agent can be selected from a range in which a content of propylene glycol in propylene glycol-containing solvent is equal to or more than 50 w/w %, preferably equal to or more than 60 w/w %, specifically preferably equal to or more than 65 w/w %. When additive amount of solubilizing agent is too much, thus propylene glycol content is reduced, stable colloid which exhibit an excellent transdermal permeability of the medicament may not be formed. It is not preferable.

Propylene glycol-containing solution can further include a hydrophilic solvent which is miscible with propylene glycol if needed. Specifically, a polyol such as glycerin, 1,3-butanediol can be exemplified in some embodiments. The content of the hydrophilic solvent is less than 10 w/w % of propylene glycol-containing solution.

Though a little amount of polyol such as glycerin or butanediol can be added to propylene glycol, it is not suitable for the colloidal liquid of the present invention to use said polyol instead of propylene glycol. For example, when phosphatidyl choline is added to glycerin, white turbidity and gathering of phosphatidyl choline toward surface of the liquid are observed, phosphatidyl choline tends to from an association colloid by itself. Additionally, it tends to gelate after medicament is added. On the other hand, phosphatidyl choline is completely dissolved into 1,3-butandiol as molecule similar to propylene glycol. However, after adding the medicament, it aggregation and precipitation tend to occur in short period, unlike in the case of propylene glycol.

In some embodiments, the liquid formulation of the present invention does not contain any hydrophobic solvent. The term "hydrophobic solvent" in this specification denotes an oleaginous solvent which doesn't dissolve in propylene glycol in arbitrary ratio. Specifically, hydrocarbons such as liquid paraffin, squalene and the like; higher fatty acids such as oleic acid, lauric acid, myristic acid, palmitic acid, stearic acid, and the like; higher alcohol such as cetyl alcohol, stearyl alcohol, myristyl alcohol, and the like; a fatty acid esters such as isopropyl myristate, isopropyl palmitate, butyl stearate, and the like; vegetable oils such as olive oil, *camellia* oil, jojoba oil, and the like cam be exemplified.

In some embodiments, the colloidal liquid formulation of the present invention contains propylene glycol at a concentration equal to or more than 60 w/w %, and consists only components which are soluble in propylene glycol or propylene glycol-containing solvent.

Various additives which are conventionally used in an external preparation or a cosmetics can be added to the liquid formulation of the present invention if necessary. Examples of the possible additives include perfumes, antioxidant agent, antiseptic agent, coloring agent, buffering agent, pH adjusting agent, an ultraviolet absorber, an antibacterial medicine, and the like can be exemplified. Examples of perfumes include ethanol, orange essence, and the like. Examples of the antioxidant agent include tocopherol acetate, edetate sodium, erythorbic acid, 1,3-butylene glycol, sodium metabisulfite, and the like. Examples of the antiseptic agent include sorbic acid, taurine, and the like. Examples of the pH adjusting agent include organic acids such as citric acid, acetic acid, acidum tartaricum, and the like; inorganic acids such as phosphoric acid, hydrochloride, chloride, and the like. Moreover, an ultraviolet absorber and an antibacterial agent can be added depending on purposes.

In some embodiments, the liquid formulation of the present invention is prepared by mixing the medicament of dissolved state in propylene glycol with phosphatidyl choline of the dissolved state in propylene glycol. If the medicament is insoluble or poorly-soluble to propylene glycol, and a desired quantity can't be dissolved, a solubilizing agent such as water, polyethylene glycol is added to form "propylene glycol-containing solvent". The medicament of dissolved state is prepared by dissolving the medicament to the propylene glycol-containing solvent. A liquid formulation exhibiting excellent transdermal permeability can be formed by mixing the medicament which is dissolved in propylene glycol or the propylene glycol-containing solvent with phosphatidyl choline or propylene glycol solution of phosphatidyl choline. The liquid formulation is usually a colloidal dispersed liquid. If the medicament is low molecule, the median particle size is observed within the range from 5 nm to 200 nm in many cases. The concentration of the solubilizing agent can be selected from a range in which ratio of propylene glycol to total weight of the liquid formulation is equal to or more than 40 weight %, preferably equal to or more than 60 weight %. The concentration of the solubilizing agent to propylene glycol can be selected, for example from 0 to 50 weight %, preferably from 0 to 35 weight %.

In some embodiments, the propylene glycol-containing solvent can further contain a hydrophilic organic solvent miscible with propylene glycol if needed. Specifically, a polyol such as glycerin, 1,3-butandiol can be exemplified. The concentration of the hydrophilic solvent is, for example, less than 30 weight % of propylene glycol-containing solvent, preferable less than 20 weight %. The concentration of the hydrophilic organic solvent relative to propylene glycol is less than 50 weight % of propylene glycol.

In some embodiments, the colloidal dispersion or liquid formulation of the present invention can be prepared by mixing the medicament of dissolved state in propylene glycol or propylene glycol-containing solvent with phosphatidyl choline of the dissolving state in propylene glycol or propylene glycol-containing solvent. When any one of the medicament or phosphatidyl choline is dissolved, it becomes a true solution, and particles with a diameter equal to or more than 10 nm is not observed. Both the medicament solution and phosphatidyl choline solution does not show Tyndall phenomenon. However, when the medicament of dissolved state is mixed with phosphatidyl choline of dissolved state, it becomes a colloidal dispersion showing Tyndall phenomenon, and the mode particle size thereof is observed around 100 nm.

As a method for mixing the medicament of dissolved state and phosphatidyl choline of dissolved state, following methods are exemplified, but are not particularly limited. That is, a method of a solution (solution I) in which medicament is dissolved in propylene glycol or propylene glycol-containing solvent and the other solution (solution II) in which phosphatidyl choline is dissolved in propylene glycol or propylene glycol-containing solvent are prepared respectively, thus mixing said solution I with said solution II; a method of adding phosphatidyl choline into said solution I and mixing it; a method of adding the medicament into said solution II and mixing it; a method of adding phosphatidyl choline and the medicament at the same time into propylene glycol or propylene glycol-containing solvent. The method in which solution I and solution II are prepared respectively and then they are mixed together is excellent in the point that it can be reliably confirmed phosphatidyl choline and the medicament are in their dissolved state. By mixing and stirring the medicament of the dissolved state with phosphatidyl choline of the dissolved state, a stable colloidal dispersing liquid having an average particle diameter of 50 to 500 nm can be obtained. In some embodiments, alkanolamine and other additives can be added at any time. In some embodiments, higher alcohol, such as oleyl alcohol and isostearyl alcohol, can be added at any time. The higher alcohol A method for adapting the liquid formulation to the skin is not particularly limited, and a method of coating with, or splaying, a method of attaching a suitable carrier carrying the liquid formulation on the skin can be exemplified. In some embodiments, a method of attaching a foamed matrix carrying the liquid formulation therein is preferable, because it has good handling property and is easy to adjust the dosage. The "foamed matrix" is a porous body obtained by forming resins with a physical or chemical procedure. Specifically, polyurethane foam can be exemplified. The "polyurethane foam" is obtained by forming polyol and polyisocyanate with polymerizing adding a bloating agent, a foam stabilizer, a catalyst, and a coloring agent. Polyurethane foam is abbreviated to urethane foam, and is broadly classified into the following three groups by foaming process. That is, a "soft urethane foam" having interconnected cells, is soft and possesses restorability; a "rigid urethane foam" having closed pores, is hard and has no resilience; a "semi-rigid urethane form" having intermediate properties. The rigid urethane foam of discontinuity type is preferable because leakage is small when it carries medicament solution.

The method for applying the liquid formulation of the present invention for the skin is not particularly restricted, and the method of coating with or spraying liquid formulation, the method of adhering a suitable carrier carrying the liquid formulation on the skin can be exemplified. Among then, the method of adhering the carrier (a nonwoven fabric, a foamed matrix, etc.) carrying the liquid formulation is preferable because, it has a good handling property and is easy to adjust the dosage.

EXAMPLES

Hereinafter, the present invention is explained in detail with examples. The present invention is not limited in any way by these examples Reference Preparation Example Phosphatidyl choline (0.5 part by weight) was dissolved to propylene glycol (94.5 part by weight), further triethanolamine (5 part by weight) was added and stirred, to obtain a clear liquid. A red laser was irradiated to the liquid, but Tyndall phenomenon was not observed. Though the particle size distribution was measured by Zeta Sizer Nano (made by Malvern Instruments, inc.), any distribution having particle size of more than was not observed. The measurement result of the particle size distribution is shown in FIG. 1.

Preparation of a Liquid Formulation Containing Galantamine (Examples 1a to 1c) and (Comparative Examples 1a to 1c)

The liquid formulations as the composition shown in Table 1 are prepared. The obtained clear solution is irradiated with a red laser beam, to observe the presence or absence of Tyndall Phenomenon. Furthermore, transdermal permeability of galantamine of the obtained liquid formulation was evaluated with the use of Franz cell. Skin used for the test was 5 weeks old hairless rats (male) abdominal excised skin, the receptor solution was (water:ethanol=9:1) solution. The results are shown in Table 1.

ability. Liquid formulation of Comparative Example 1c containing polyethylene glycol instead of propylene glycol did not show Tyndall phenomenon, and didn't exhibit improvement of skin permeability.

Figure 2:
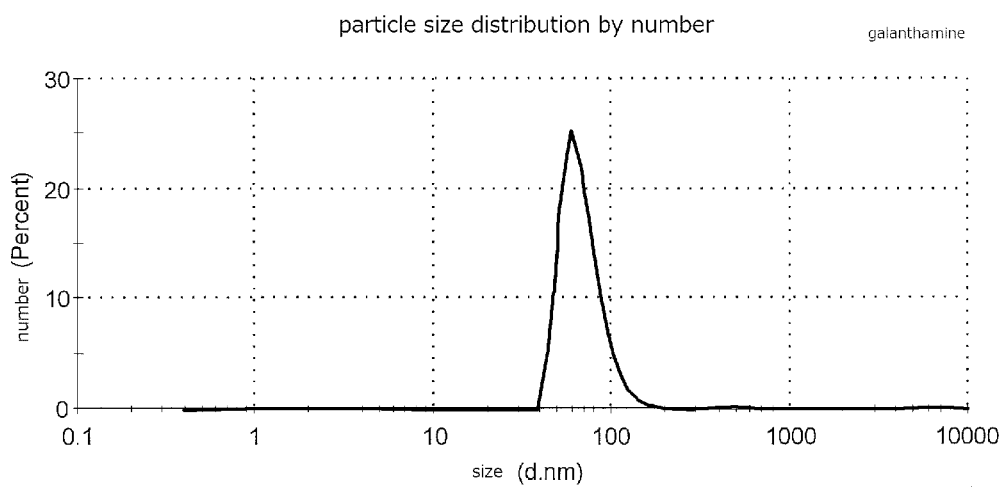
FIG. 2 shows the particle size distribution of the colloidal liquid formulation containing galantamine hydrobromide prepared in Example 1c.
Figure 3:
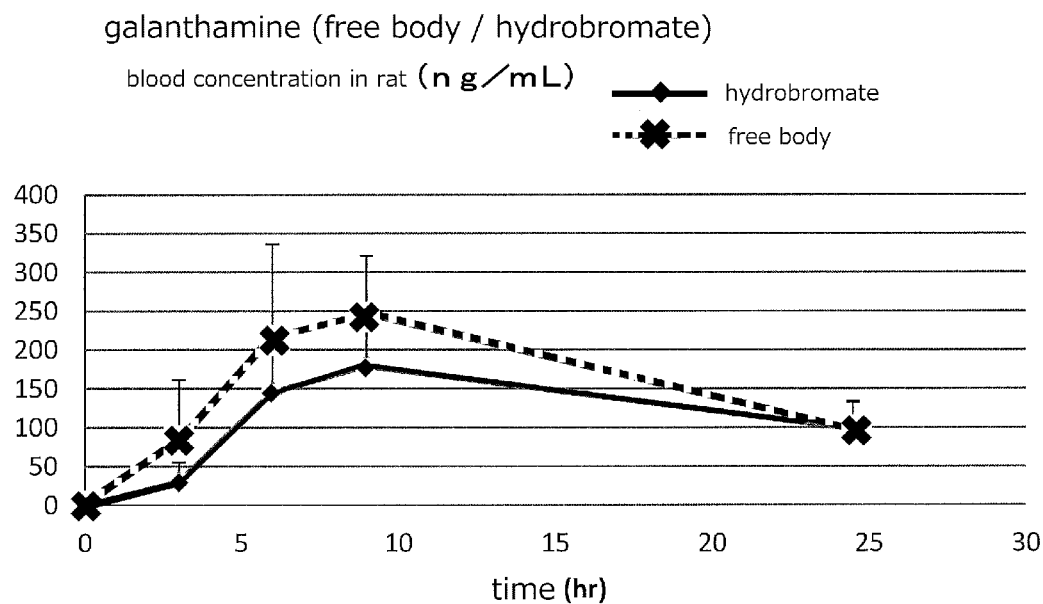
FIG. 3 is a graph showing the result of the blood concentration evaluation test of the colloidal liquid formulation containing galantamine prepared in Examples 1b and 1c.

Particle size distribution of liquid formulation of Example 1c was measured by Zeta Sizer Nano (made by Malvern Instruments, inc.). Mode of the particle size was observed at around 70 nm. The measurement result is shown in FIG. 2. Liquid formulation of Example 1b and Example 1c (0.08 g) was impregnated into urethane foam (area: 2 $cm^2$ thickness: 0.5 mm bulk density: 0.2 $g/3\ cm^3$) to prepare liquid type adhesive patch. Prepared liquid type adhesive patch were adhered to back of rats (5 weeks old, male) and transition of blood concentration in rats was evaluated according to conventional method. The result is shown in FIG. 3. Both the liquid formulation of Example 1c containing free galanthamine and the liquid formulation of Example 1c containing hydrobromate exhibit excellent transdermal absorbability, and there was no difference in the transition of blood concentration.

TABLE 1

|  | Ex. 1a | Ex. 1b | Com. 1a | Com. 1b | Ex. 1c | Com. 1c |
| --- | --- | --- | --- | --- | --- | --- |
| galantamine | 5.0 | 5.0 | 5.0 | 5.0 | — | — |
| galantamine HBr | — | — | — | — | 4.0 | 4.0 |
| PG | 94.5 | 89.5 | 90.0 | 89.5 | 70.5 | — |
| PEG | — | — | — | — | — | 61.5 |
| purified water | — | — | — | — | 20.0 | 30.0 |
| PC | 0.5 | 0.5 | — | — | 0.5 | 0.5 |
| lysolecithin | — | — | — | 0.5 | — | — |
| TEA | — | 5.0 | 5.0 | 5.0 | 4.0 | 4.0 |
| total | 100 | 100 | 100 | 100 | 100 | 100 |
| Presence or absence of Tyndall phenomenon | presence | presence | absence | absence | presence | absence |
| Comulative skin permeation amount at 6 hours ($\mu g/cm^2$) | 208 | 359 | 15 | 37 | 226 | 18 |

PG: propylene glycol
PEG: polyethylene glycol
PC: phosphatidyl choline
TEA: triethanolamine Liquid formulation of Example 1a containing phosphatidyl choline showed excellent skin permeability compared to liquid formulation of Comparative Example 1a containing no phosphatidyl choline. Liquid formulation of Example 1b further containing ethanolamine showed superior skin permeability to liquid formulation of Example 1a. Liquid formulation of Comparative Example 1b containing lysolecithin instead of phosphatidyl choline didn't show Tyndall phenomenon, and didn't exhibit improvement of skin permeability. Galanthamine hydrobromide has low solubility to propylene glycol. Therefore, it was dissolved to propylene glycol-containing solvent in which purified water was added as solubilizing agent, thus prepared colloidal liquid with the same procedure as free galanthamine (Example 1c). The obtained liquid formulation exhibited excellent skin perme- Preparation of Liquid Formulation Containing Ramelteon (Example 2a) and (Comparative Examples 2a to 2e)

Figure 4:
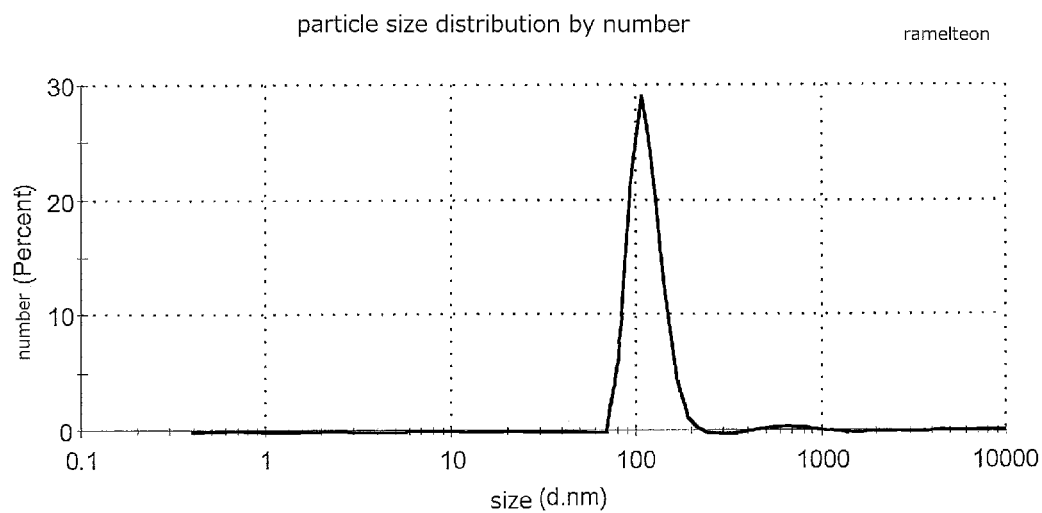

The liquid formulations as the composition (w/w %) shown in Table 2 are prepared. Skin permeability of Ramelteon was evaluated by Franz cell for obtained liquid formulation. The results is shown in Table 2. The particle size distribution was measured by Zeta Sizer Nano (made by Malvern Instruments, inc.) for liquid formulation of 2a. Mode of the particle size was observed at around 110 nm. The result is shown in FIG. 4. Skin used in the Franz cell test was abdominal excised skin of 5 weeks old hairless rats (male), and the receptor solution was (water:ethanol=9:1) solution.

TABLE 2

|  | Ex. 2a | Com. 2a | Com. 2b | Com. 2c | Com. 2d | Com. 2e |
|---|---|---|---|---|---|---|
| Ramelteon | 5.0 | 5.0 | 5.0 | 10.0 | 5.0 | 5.0 |
| PG | 89.5 | 89.5 | 89.5 | 90.0 | 90.0 | 90.0 |
| PC | 0.5 | — | — | — | — | — |
| Tween80 | — | 0.5 | — | — | — | — |
| HCO40 | — | — | 0.5 | — | — | — |
| TEA | 5.0 | 5.0 | 5.0 | — | — | 5.0 |
| Palmitic acid | — | — | — | — | 5.0 | — |
| total | 100 | 100 | 100 | 100 | 100 | 100 |
| Presence or absence of Tyndall phenomenon | presence | absence | absence | absence | absence | absence |
| Comulative skin permeation amount ($\mu g/cm^2$) at 6 hours | 72 | 23 | 19 | — | 7 | 13 |
| Comulative skin permeation amount ($\mu g/cm^2$) at 24 hours | 1324 | 211 | 197 | 12 | 91 | 112 |

PG: propylene glycol
PC: phosphatidyl choline
POC40: Polyoxyethylene hardened castor oil
TEA: triethanolamine All the liquid formulations of Comparative Examples 2a to 2e did not form colloidal liquid, and had poor skin permeability. Comparative Examples 2a and 2b contain Tween80 and HCO40 instead of phosphatidyl choline. They are same as phosphatidyl choline at the point having surface activity. However, both the Comparative Example 2a and 2b did not form colloidal liquid and did not show significant improvement in skin permeability. Therefore, phosphatidyl choline possesses a peculiar transdermal absorption promoting activity different from any other usual surfactant.

Figure 5:
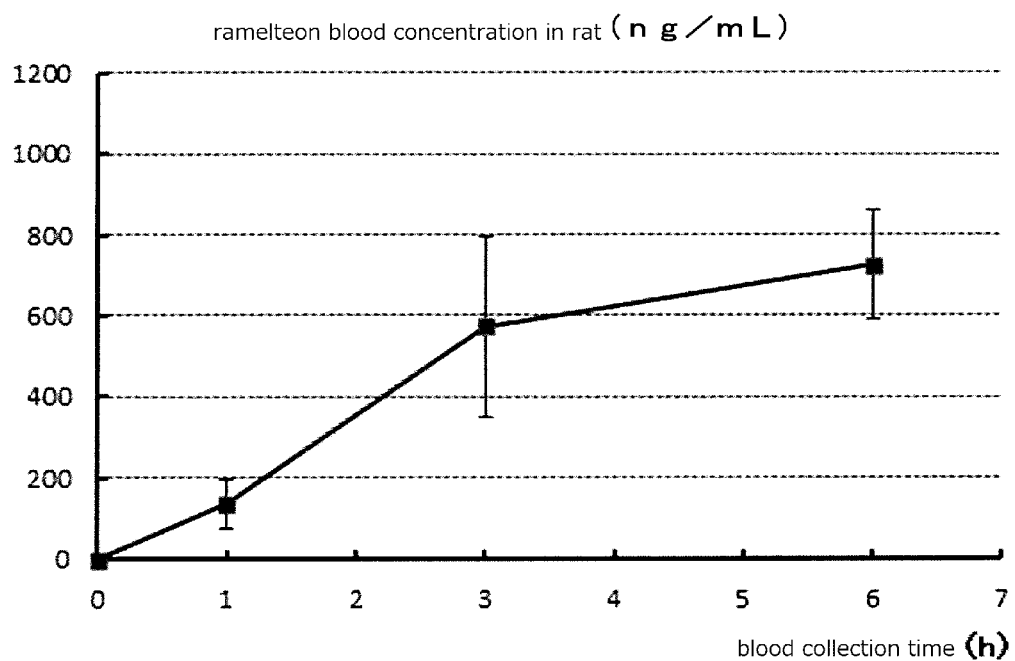

Liquid formulation of Example 2a (0.3 g) was impregnated into urethane foam (area: 9 cm² thickness: 0.5 mm bulk density: 0.2 g/3 cm³) to prepare liquid type adhesive patch. Prepared liquid type adhesive patch were adhered to back of rats (5 weeks old, male) and transition of blood concentration in rats was evaluated according to conventional method. The result is shown in FIG. 5. The adhesive patches which had been adhered to rat for 6 hors were collected to measure amount of ramelteon remaining in the adhesive patch and surface of the skin. Residual ration of ramelteon was about 65%. Namely, about 35% of ramelteon contained in the adhesive patch was transferred into the blood. The discharge rate of ramelteon was about 5.5 mg/sheet.

Examination of Content of Phosphatidyl Choline and Absorption Promoter

The liquid formulations as the composition (w/w %) shown in Table 3 are prepared. Skin permeability of was evaluated by Franz cell for each liquid formulations. The results are shown in Table 3. Skin used in the Franz cell test was abdominal excised skin of 5 weeks old hairless rats (male), and the receptor solution was (water:ethanol=9:1) solution.

TABLE 3

|  | Ex. 2a | Ex. 2a | Ex. 2c | Ex. 2d | Ex. 2e | Ex. 2f |
|---|---|---|---|---|---|---|
| Ramelteon | 5.0 | 5.0 | 5.0 | 5.0 | 5.0 | 5.0 |
| PG | 89.75 | 89.5 | 87.0 | 87.0 | 89.5 | 89.5 |
| PC | 0.25 | 0.5 | 3.0 | 3.0 | 0.5 | 0.5 |
| TEA | 5.0 | 5.0 | 5.0 | — | — | — |
| DEA | — | — | — | — | 5.0 | — |
| DIPA | — | — | — | — | — | 5.0 |
| Palmitic acid | — | — | — | 5.0 | — | — |
| Presence or absence of Tyndall phenomenon | presence | presence | presence | presence | presence | presence |
| total | 100 | 100 | 100 | 100 | 100 | 100 |
| Comulative skin permeation amount ($\mu g/cm^2$) at 6 hours | 26 | 72 | 88 | 17 | 18 | 32 |
| Comulative skin permeation amount ($\mu g/cm^2$) at 24 hours | 826 | 1324 | 1153 | 239 | — | — |

PG: propylene glycol
PC: phosphatidyl choline
TEA: triethanolamine
DEA: diethanolamine
DIPA: diisopropanolamine The skin permeation amount increased depending on content of phosphatidyl choline. However, a marked increase in skin permeability was not observed with the addition of phosphatidyl choline exceed 0.5 w/w %. Therefore, the content of Phosphatidyl choline is usually selected from in the range of 0.1 to 5 w/w %, preferably 0.3 to 2.0 w/w %. Triethanolamine exhibits significant skin permeation accelerated effect in shorter period compare to the other absorption promoters such as diethanolamine, diisopropanolamine, and the like.

Examination of Content of Absorption Promoter

Examples 2 g to 2j

The liquid formulations as the composition (w/w %) shown in Table 4 are prepared. Skin permeability of was evaluated by Franz cell for each liquid formulations. The results are shown in Table 4. Skin used in the Franz cell test was abdominal excised skin of 5 weeks old hairless rats (male), and the receptor solution was (water:ethanol=9:1) solution.

TABLE 4

|  |  | Ex. 2g | Ex. 2h | Ex. 2i | Ex. 2a | Ex. 2j |
|---|---|---|---|---|---|---|
| Ramelteon |  | 5.0 | 5.0 | 5.09 | 5.0 | 5.0 |
| PG |  | 94.0 | 93.5 | 91.5 | 89.5 | 54.5 |
| PC |  | 0.5 | 0.5 | 0.5 | 0.5 | 0.5 |
| TEA |  | 0.5 | 1.0 | 3.0 | 5.0 | 10.0 |
| total |  | 100 | 100 | 100 | 100 | 100 |
| Comulative skin permeation amount ($\mu g/cm^2$) | at 6 hours | 13 | 20 | 55 | 72 | 58 |
|  | at 24 hours | 438 | 720 | 1146 | 1324 | 1103 |

PG: propylene glycol
TEA: triethanolamine
PC: phosphatidyl choline

The skin permeation amount increased depending on the amount of triethanolamine. The content of triethanolamine can be selected from 0.01 to 10 w/w %. In order to obtain a sufficient absorption promoting effect, it is preferably 1 to 8 w/w %, particularly preferably 2.5 to 5.5 w/w %.

Preparation of Liquid Formulations Containing Various Medicaments (Examples 3 to 7b) and (Comparative Examples 3 to 7)

Figure 6:
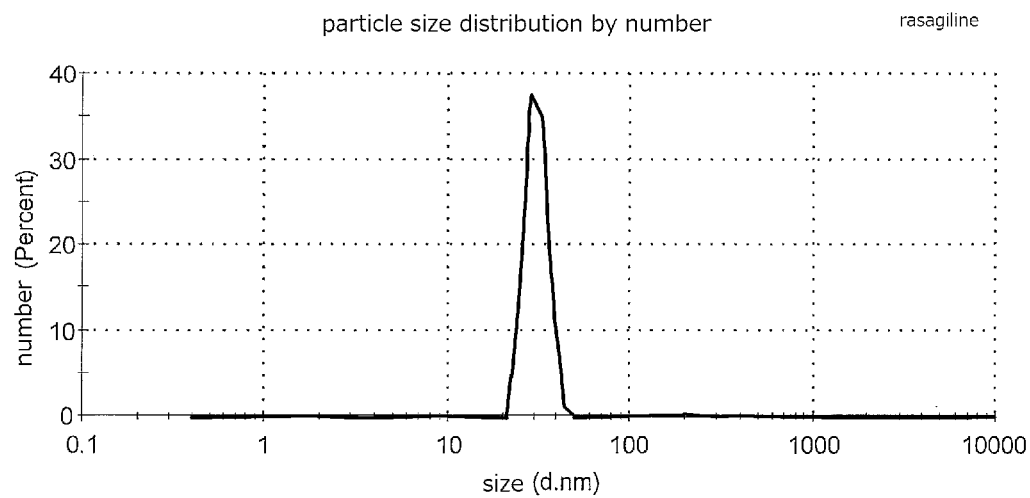
FIG. 6 shows the particle size distribution of the colloidal liquid formulation containing rasagiline prepared in Example 3.
Figure 7:
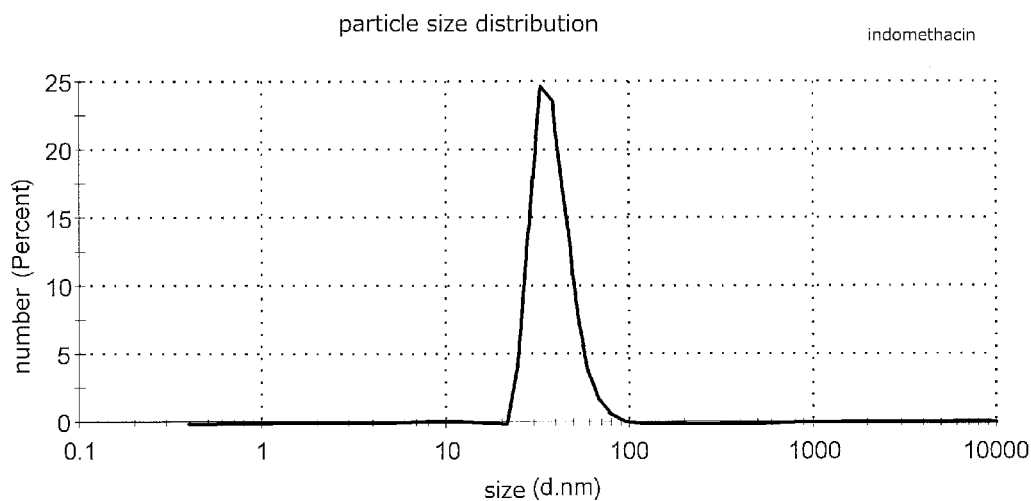
FIG. 7 shows the particle size distribution of the colloidal liquid formulation containing indomethacin prepared in Example 5.

The liquid formulations as the composition (w/w %) shown in Table 5 and Table 6 are prepared. Skin permeability of was evaluated by Franz cell for each liquid formulations. The results are shown in Table 5 and Table 6. The particle size distribution was measured by Zeta Sizer Nano (made by Malvern Instruments, inc.). The results are shown in FIG. 6 and FIG. 7. Skin used in the Franz cell test was abdominal excised skin of 5 weeks old hairless rats (male), and the receptor solution was (water:ethanol=9:1) solution.

TABLE 5

|  |  | Ex. 3 | Com. 3 | Ex. 4 | Com. 4 | Ex. 5 | Com. 5 | Ex. 6 | Com. 6 |
|---|---|---|---|---|---|---|---|---|---|
| Rasagiline mesylate |  | 6.25 | 6.25 | — | — | — | — | — | — |
| Escitalopram maleate |  | — | — | 2.0 | 2.0 | — | — | — | — |
| Indomethacin |  | — | — | — | — | 0.5 | 0.5 | — | — |
| Donepezil hydrochloride |  | — | — | — | — | — | — | 5.0 | 5.0 |
| PG |  | 88.25 | 88.75 | 92.5 | 93.0 | 99.0 | 99.5 | 78.3 | 79.3 |
| Purified water |  | — | — | — | — | — | — | 15.0 | 15.0 |
| PC |  | 0.5 | — | 0.5 | — | 0.5 | — | 1.0 | — |
| TEA |  | 5.0 | 5.0 | 5.0 | 5.0 | — | — | 0.5 | 0.5 |
| Sodium pyrosulfite |  | — | — | — | — | — | — | 0.2 | 0.2 |
| total |  | 100 | 100 | 100 | 100 | 100 | 100 | 100 | 100 |
| Presence or absence of Tyndall phenomenon |  | presence | absence | presence | absence | presence | absence | presence | absence |
| Comulative skin permeation amount ($\mu g/cm^2$) | at 2 hours | 93 | 24 | — | — | — | — | — | — |
|  | At 6 hours | — | — | 45 | 0 | — | — | 77 | 3 |
|  | at 24 hours | — | — | — | — | 282 | 57 | — | — |

PG: propylene glycol
PC: phosphatidyl choline
TEA: triethanolamine

TABLE 6

|  |  | Ex. 7a | Ex. 7b | Com. 7 |
|---|---|---|---|---|
| Apomorphine HCL |  | 3.0 | 3.0 | 3.0 |
| PG |  | 96.3 | 95.8 | 96.8 |
| PC |  | 0.5 | 0.5 | — |
| TEA |  | — | 0.5 | — |
| Sodium pyrosulfite |  | 0.2 | 0.2 | 0.2 |
| total |  | 100 | 100 | 100 |
| Presence or absence of Tyndall phenomenon |  | presence | presence | absence |
| Comulative skin permeation amount ($\mu g/cm^2$) | at 6 hours | 20 | 50 | 0 |
|  | at 24 hours | 459 | 1428 | 0 |

PG: propylene glycol
PC: phosphatidyl choline
TEA: triethanolamine

At all the medicament, colloidal liquid formulations containing phosphatidyl choline showed marked improvement in skin permeation amount compared to liquid formulation containing no phosphatidyl choline. Addition of triethanolamine caused further dramatic increase in skin permeation amount. The colloidal liquid formulation of the present invention exhibits excellent transdermal permeation for any of basic medicament acidic medicament, and neutral medicament.

Figure 8:
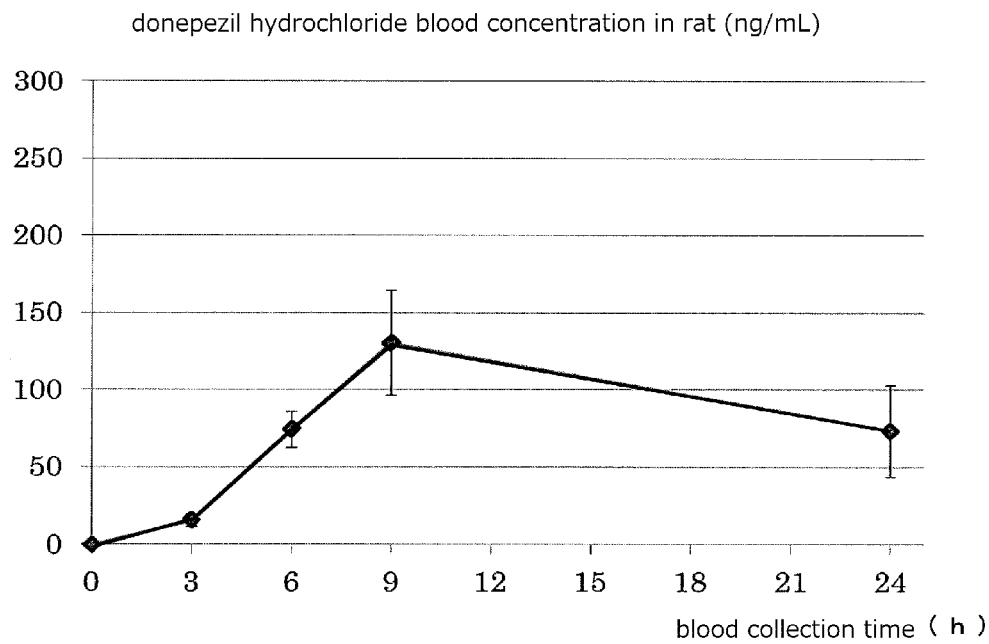
FIG. 8 is a graph showing the result of the blood concentration evaluation test of the colloidal liquid formulation containing donepezil prepared in Example 6.
Figure 9:
FIG. 9 is a photograph of the liquid type adhesive patch used in the blood concentration evaluation test.

Liquid formulation of Example 6 (0.18 g) was impregnated into urethane foam (area: 6 cm$^2$ thickness: 0.5 mm bulk density: 0.2 g/cm$^3$) to prepare liquid type adhesive patch. Prepared liquid type adhesive patch were adhered to back of rats (5 weeks old, male) and transition of blood concentration in rats was evaluated according to conventional method. The result is shown in FIG. 8. Though skin irritation caused by donepezil has been reported, any indication such as erythema was not observed at all on the skin of rats after the adhesive patch were peeled off. It is presumed to be due to skin protective effect of phosphatidyl choline.

Liquid Formulation Containing Rizatriptan

Figure 10:
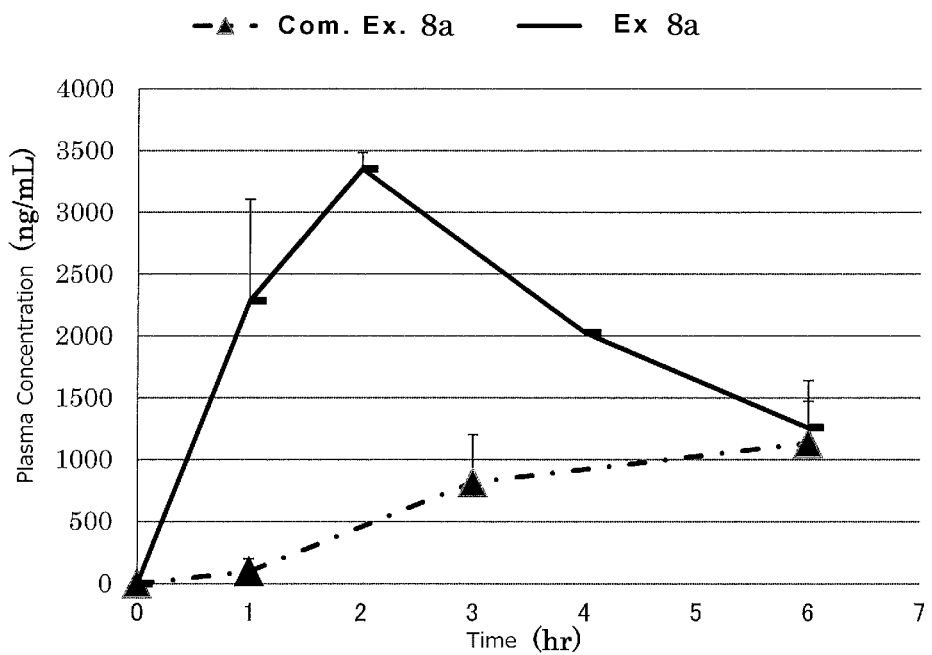
FIG. 10 is a graph showing the result of the in vivo rizatriptan plasma concentration evaluation test of the liquid formulation of Example 1-1 and Comparative example 1-1 using rat.

The liquid formulations as the composition shown in Table 7 were prepared. In vivo plasma concentration was evaluated to the obtained liquid formulation using rat. Plasma concentration of rizatriptan (ng/ml) at each blood collection point are shown in Table 7. A graph showing transition of plasma concentration is shown in FIG. 10.

and the plasma concentration achieved its peak after 2 hours. In the Liquid formulation of the comparative example which does not contain oleyl alcohol, only a small amount of the medicament transitioned to plasma despite the adhering area was broad, and the dosage amount was large. Moreover, its transdermal penetration lag time was long.

Liquid Formulation Containing Memantine and Donepezil

The liquid formulations as the composition shown in Table 8 were prepared. Transdermal permeability of donepezil and memantine of the obtained liquid formulation was evaluated with the use of Franz cell. Skin used for the test was Yucatan micro pig (male 5 months old) skin, and the receptor solution was (water:ethanol=9:1) solution. Cumulative skin permeation amounts (µg/cm$^2$) after 7 hours are shown in Table 8.

Figure 11:
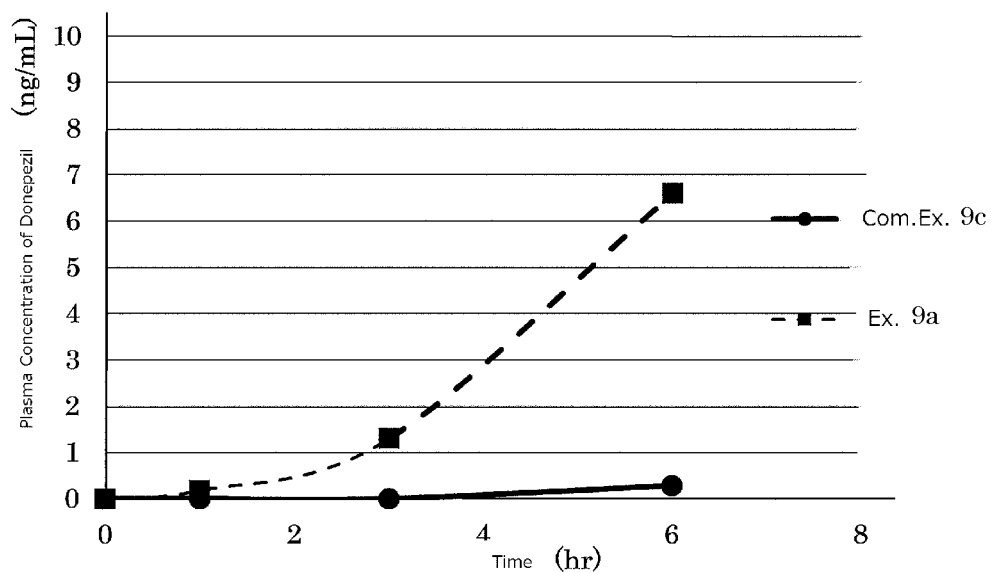
FIG. 11 is a graph showing the result of the in vivo donepezil plasma concentration evaluation test of the liquid formulation of Example 1-1 and Comparative example 1-3 using miniature pig.

In vivo plasma concentration was evaluated for the liquid preparation obtained in Example 9a and Comparative Example 9c using miniature pig. A graph showing transition of the blasma concentration is shown in FIG. 11.

The testing condition was as follows;
Animal Species: miniature pig
Dosage Amount: Example 9a medicament liquid 6 g/100 cm$^2$ (donepezil 300 mg)
Comparative Example 9c medicament liquid 6 g/100 cm$^2$ (donepezil 300 mg)
Measuring Means: HPLC

TABLE 8

|  |  | Ex. 9a | Ex. 9b | Ex. 9c | Com. 9a | Com. 9b | Com. 9c |
| --- | --- | --- | --- | --- | --- | --- | --- |
| Donepezil hydrochloride |  | 5.0 | 5.5 | — | 5.5 | 5.5 | 5.5 |
| Memantine hydrochloride |  | 10.0 | 6.0 | 6.0 | 6.0 | 6.0 | — |
| Propylene glycol |  | 68.2 | 50.0 | 72.0 | 69.5 | 66.7 | 78.1 |
| 1,3-butanediol |  | — | — | 16.6 | — | — | — |
| Phosphatidyl choline |  | 0.2 | 0.3 | 0.5 | 0.7 | — | 0.8 |
| triethanolamine |  | 0.8 | 0.8 | 0.4 | 1.3 | 1.0 | 0.6 |
| Purified water |  | 15.0 | 5.0 | 3 | 17 | 20 | 15.0 |
| Oleyl alcohol |  | 0.8 | — | 1.5 | — | 0.8 | — |
| Isostearyl alcohol |  | — | 2.4 | — | — | — | — |
| Total |  | 100 | 100 | 100 | 100 | 100 | 100 |
| Cumulative skin permeation amount after 6 hr (µg/cm$^2$) | Donepezil | 9.7 | 8.4 | — | 1.4 | 3.1 | 0.5 |
|  | memantine | 86.6 | 47.7 | 43.2 | 4.1 | 9.3 | — |

The testing condition was as follows;
Animal Species: hairless rat (HWY/Slc) 5 weeks old
Dosage Amount: Example 8a medicament liquid 0.06 g/2 cm$^2$ (rizatriptan 12 mg)
Comparative Example 8a medicament liquid 0.27 g/9 cm$^2$ (rizatriptan 27 mg)
Measuring Means: HPLC

TABLE 7

|  |  | Ex. 8a | Com. 8a |
| --- | --- | --- | --- |
| Rizatriptan |  | 20 | 10 |
| Propylene glycol |  | 76.5 | 84.5 |
| Phosphatidyl choline |  | 0.5 | 0.5 |
| Oleyl alcohol |  | 2.5 | 0 |
| triethanolamine |  | 0.5 | 5 |
| total |  | 100 | 100 |
| Plasma concentration of rizatriptan (ng/ml) | 1 hour | 2286 | 99.8 |
|  | 2 hour | 3353 | — |
|  | 3 hour | — | 817.3 |
|  | 4 hour | 2027 | — |
|  | 6 hour | 1258 | 1135 |

In the liquid formulation of the present invention including oleyl alcohol, rizatriptan transitioned to plasma rapidly, It was confirmed that the liquid formulation of Example 9a containing oleyl alcohol and the liquid formulation or Example 9b containing isostearyl alcohol increased transdermal permeability in a short time of 7 hors compared to the liquid formulation of Comparative Example 9a containing none of oleyl alcohol and isostearyl alcohol, and the liquid formulation of Comparative Example 9b containing oleyl alcohol but no phosphatidyl choline. The combination of a higher alcohol and phosphatidyl choline generated a synergy effect, thus the transdermal permeability in a short time was significantly improved.

A Liquid Formulation Containing Memantine

The liquid formulations as the compositions (weight %) shown in Table 9 ware prepared. Transdermal permeability of memantine of the obtained liquid formulation was evaluated with the use of Franz cell. Skin used for the test was 5 weeks old hairless rats (mail) abdominal excised sin, and the receptor solution was (water:ethanol=9:1) solution. Cumulative skin permeation amounts (µg/cm$^2$) after 6 hours are shown in Table 9.

TABLE 9

|  | Ex. 10a | Ex. 10b | Ex. 10c | Ex. 10c | Ex. 10e | Com. 10a |
|---|---|---|---|---|---|---|
| Memantine hydrochloride | 5.0 | 5.0 | 5.0 | 5.0 | 6.0 | 5.0 |
| Phosphatidyl choline | 0.1 | 0.25 | 0.5 | 1.0 | 0.5 | 0 |
| Propylene glycol | 87.1 | 86.95 | 86.7 | 86.2 | 72 | 87.2 |
| 1,3-butanediol | — | — | — | — | 16.6 | — |
| triethanolamine | 0.4 | 0.4 | 0.4 | 0.4 | 0.4 | 0.4 |
| Isostearyl alcohol | 2.4 | 2.4 | 2.4 | 2.4 | — | 2.4 |
| Oleyl alcohol | — | — | — | — | 1.5 | — |
| Purified water | 5 | 5 | 5 | 5 | 3 | 5 |
| Total | 100 | 100 | 100 | 100 | 100 | 100 |
| Cumulative skin permeation amount after 6 hr | 1048 | 1484 | 1600 | 1455 | 1927 | 358 |

The liquid formulation of Example 10a to Example 10e containing both phosphatidyl choline and isostearyl or oleyl alcohol exhibited excellent transdermal permeability in the vitro test. Therefore, it was estimated that memantine should be also permeated through the skin in skin irritation study in rabbits. However, the skin irritation was minor. In contrast, the liquid formulation of Comparative Example 10a containing no phosphatidyl choline caused strong skin irritation relative to the liquid formulations of Example 10a to 10e, despite they showed lower permeability.

Comparative Formulation

A publicly known transdermal preparation containing memantine (described in Japanese Patent Publication No. 2009-13171) was prepared in a manner as follows;

| Memantine hydrochloride | 20/0% |
|---|---|
| Sodium hydroxide | 3.7% |
| An acrylic adhesive having hydroxyl group | 76.3% |

Aqueous solution of sodium hydroxide was added to memantine hydrochloride which were weighted at the above ratio and mixed. Acrylic adhesive having hydroxyl group was added to it, and was coated on a about 100 μm-thick support, and dried to produce a patch preparation.

In Vitro Transdermal Permeability Test Using Human Skin/Prima Skin Irritation Test in Rabbits The liquid preparation of Example 10f as the composition shown in Table 10 was prepared. In vitro transdermal permeability test using human skin was conducted for the liquid preparation of Example 1 Of and the comparative formulation.

In the skin irritation test, a piece of urethane form impregnated with the liquid formulation of Example 10f (0.03 g/cm$^2$) was used as a test preparation. They were applied on rabbits (Kbl: JW male 8 weeks old) for 24 hours. Skin condition was confirmed visually at 1, 24, and 48 hours later after the removal of test preparations, and the primary skin irritation was evaluated by the Draize test. Primary irritation index (P.I.I.) are shown in Table 10.

TABLE 10

|  | Ex. 10f | Com. 10f |
|---|---|---|
| Memantine hydrochloride | 5.0 | |
| Phosphatidyl choline | 0.42 | |
| propylene glycol | 87.3 | |
| triethanolamine | 0.4 | |

TABLE 10-continued

|  | Ex. 10f | Com. 10f |
|---|---|---|
| isostearyl alcohol | 1.2 | |
| Oleyl alcohol | 0.68 | |
| water | 5 | |
| total | 100 | |
| cumulative human skin permeation amount (μg/cm$^2$) | 991.8 | 529.7 |
| P.I.I. | 0.7 | 2 |

In the liquid formulation of Example 10f, it was estimated that memantine was permeated through skin, because the liquid formulation exhibits excellent transdermal permeability in the vitro test. However the skin irritation was slight.

A Liquid Formulation Containing Tramadol

Figure 12:
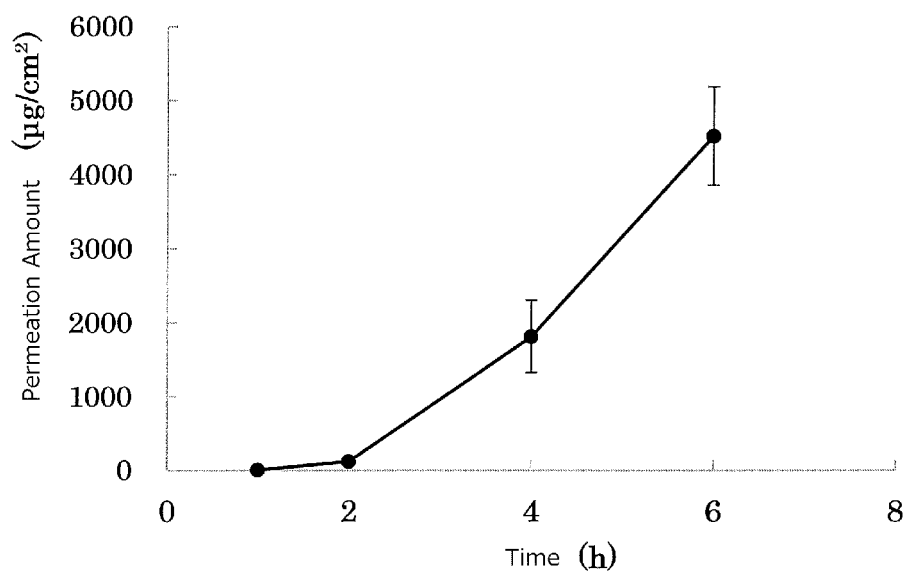
FIG. 12 is a graph showing the result of the in vitro skin permeability test of the liquid formulation of Example 4-1 using rat skin.

Liquid formulations as the compositions (weight %) are shown in Table 11. Transdermal permeability of tramadol was evaluated for the obtained liquid formulation with use of Franz cell. The skin used for the test was 5 weeks old hairless rats abdominal excised skin, the receptor solution was (water:ethanol=9:1) solution. Cumulative skin permeation amount (μg/cm$^2$) 6 hours later from start of the test is shown in Table 11. A graph showing transition of the cumulative skin permeation amount is shown in FIG. 12.

Pieces of urethane form impregnated with the obtained liquid formulations (2×2 cm$^2$: 0.03 g/cm$^2$) were applied on rabbits (Kbl: JW male 8 weeks old) for 24 hours. Skin condition was confirmed visually at 1, 24, and 48 hours later after removal of test preparations, and the primary skin irritation was evaluated by the Draize test. Primary irritation index (P.I.I.) are shown in Table 11.

TABLE 11

|  |  | Ex. 11a |
|---|---|---|
| Tramadol hydrochloride |  | 10 |
| Phosphatidyl choline |  | 0.5 |
| Propylene glycol |  | 85.5 |
| triethanolamine |  | 1.5 |
| Oleyl alcohol |  | 1 |
| water |  | 1.5 |
| total |  | 100 |
| cumulative skin permeation amount (μg/cm$^2$) | 4 hr | 1815.6 |
|  | 6 hr | 4523.4 |
| P.I.I. |  | 0 |

The liquid formulation of the present invention containing tramadol showed extremely high permeability of 1815.6 μg/cm$^2$ in 4 hours, and 4523.4 μg/cm$^2$ in 6 hours in short time. Further, skin irritation was not confirmed in the primary skin irritation test in rabbits.

INDUSTRIAL APPLICABILITY

The colloidal liquid formulation of the present invention can be used as a liquid preparation for administering a variety of medicament transdermally.

What is claimed is:

1. A transdermal absorptive colloidal liquid formulation consisting of:
   memantine or a salt thereof,
   propylene glycol,
   phosphatidyl choline,
   an alkanolamine,
   a higher alcohol,
   water,
   a hydrophilic solvent, and
   a pH adjusting agent,
   wherein
   the propylene glycol has a concentration in a range of 50 w/w % to 99 w/w % based on a total amount of the transdermal absorptive liquid formulation.

2. The transdermal absorptive colloidal liquid formulation of claim 1, wherein the higher alcohol is oleyl alcohol and/or isostearyl alcohol.

3. The transdermal absorptive colloidal liquid formulation of claim 1, wherein an amount of the higher alcohol is 0.1 to 10 weight % based on a total weight of the transdermal absorptive liquid formulation.

4. The transdermal absorptive colloidal liquid formulation of claim 1, wherein an amount of the higher alcohol is 0.2 to 5 weight % based on a total weight of the transdermal absorptive liquid formulation.

5. The transdermal absorptive colloidal liquid formulation of claim 1, wherein an amount of the propylene glycol is 50 to 98 weight % based on a total weight of the transdermal absorptive liquid formulation.

6. The transdermal absorptive colloidal liquid formulation of claim 1, wherein an amount of the propylene glycol is 60 to 90 weight % based on a total weight of the transdermal absorptive liquid formulation.

7. The transdermal absorptive colloidal liquid formulation of claim 1, wherein an amount of the phosphatidyl choline is 0.1 to 5 weight % based on a total weight of the transdermal absorptive liquid formulation.

8. A transdermal absorptive colloidal liquid formulation consisting essentially of:
   memantine or a salt thereof,
   propylene glycol,
   phosphatidyl choline,
   an alkanolamine,
   a higher alcohol selected from the group consisting of cetyl alcohol, stearyl alcohol, myristyl alcohol, oleyl alcohol and isostearyl alcohol,
   water,
   a hydrophilic solvent selected from the group consisting of glycerin and 1,3-butanediol, and
   a pH adjusting agent,
   wherein
   the propylene glycol has a concentration in a range of 50 w/w % to 99 w/w % based on a total amount of the transdermal absorptive liquid formulation.

9. The transdermal absorptive colloidal liquid formulation of claim 8, wherein the higher alcohol is oleyl alcohol and/or isostearyl alcohol.

10. The transdermal absorptive colloidal liquid formulation of claim 8, wherein an amount of the higher alcohol is 0.1 to 10 weight % based on a total weight of the transdermal absorptive liquid formulation.

11. The transdermal absorptive colloidal liquid formulation of claim 8, wherein an amount of the higher alcohol is 0.2 to 5 weight % based on a total weight of the transdermal absorptive liquid formulation.

12. The transdermal absorptive colloidal liquid formulation of claim 8, wherein an amount of the propylene glycol is 50 to 98 weight % based on a total weight of the transdermal absorptive liquid formulation.

13. The transdermal absorptive liquid formulation of claim 8, wherein an amount of the propylene glycol is 60 to 90 weight % based on a total weight of the transdermal absorptive liquid formulation.

14. The transdermal absorptive colloidal liquid formulation of claim 8, wherein an amount of the phosphatidyl choline is 0.1 to 5 weight % based on a total weight of the transdermal absorptive liquid formulation.

* * * * *